US011318153B2

(12) United States Patent
Lin et al.

(10) Patent No.: US 11,318,153 B2
(45) Date of Patent: May 3, 2022

(54) METHOD OF USING NEOANDROGRAPHOLIDE FOR LOWERING BLOOD SUGAR, LOWERING BLOOD LIPID, IMPROVING LIVER FUNCTION AND IMPROVING RENAL FUNCTION

(71) Applicant: Bioalpha International Sdn. Bhd., Selangor (MY)

(72) Inventors: Yu-Chin Lin, Yilan County (TW); Ching-Wen Chang, Yilan County (TW)

(73) Assignee: Bialpha International Sdn. Bhd., Selangor (MY)

( * ) Notice: Subject to any disclaimer, the term of this patent is extended or adjusted under 35 U.S.C. 154(b) by 0 days.

(21) Appl. No.: 16/449,347

(22) Filed: Jun. 22, 2019

(65) Prior Publication Data
US 2019/0388446 A1    Dec. 26, 2019

(30) Foreign Application Priority Data

Jun. 25, 2018 (TW) ................. 107121756
Jun. 25, 2018 (TW) ................. 107121758
Jun. 25, 2018 (TW) ................. 107121759

(51) Int. Cl.
*A61K 31/704* (2006.01)
*A61P 13/12* (2006.01)
*A61P 1/16* (2006.01)
*A61P 3/10* (2006.01)

(52) U.S. Cl.
CPC .............. *A61K 31/704* (2013.01); *A61P 1/16* (2018.01); *A61P 3/10* (2018.01); *A61P 13/12* (2018.01)

(58) Field of Classification Search
CPC .................................................. A61K 31/704
See application file for complete search history.

(56) References Cited

U.S. PATENT DOCUMENTS 9,060,994 B2    6/2015    Hancke Orozco et al.

FOREIGN PATENT DOCUMENTS

| CN | 102247356 | 9/2013 |
| CN | 103766901 | 5/2014 |
| CN | 103766901 A * | 5/2014 |
| TW | 201726155 | 8/2017 |
| TW | 201737907 | 11/2017 |

OTHER PUBLICATIONS

Subramanian, R. et al., Pharmaceutical Biology, "Effectof Andrographolide and Ethanol Extractor Andrographis paniculata on Liver Glycolytic, Gluconeogenic, and Lipogenic Enzymes in a Type 2 Diabetic Rat Model", 2008, vol. 46, No. 11, pp. 772-780 (Year: 2008).*

Yang, T. et al., Phytotherapy Research, "Hypolipidemic Effects or Andrographolide and Neoandrographolide in Mice and Rats", 2013, vol. 27, pp. 618-623 (Year: 2013).*
Chen et al., machine translation of CN103766901A, originally published 2014, Google machine translation obtained Feb. 5, 2021, 9 pages (Year: 2014).*
Nair, AB, J. Basic. Clin. Pharma., "A simple practice guide for dose conversion between animals and humans", 2016, vol. 7, pp. 27-31 (Year: 2016).*
Chao, Wen-Wan et al., Chinese Medicine, "Isolation and identification of bioactive compounds in *Andrographis paniculata* (Chuanxinlian)" 2010, vol. 5, 15 pages (Year: 2010).*
Chen, Wei et al., Translation of CN103766901 (originally published 2014), "Application of neoandrographolide to preparation of diet foods of pharmaceuticals", translation obtained by the U.S.P.T.O. Apr. 2021, translated by Schreiber Translations, Inc. (Year: 2014).*
Zhao, Jingxiang et al., Phytochemical Analysis, "Determination of Andrographolide, Deoxyandrographolide and Neoandrographolide in the Chinese Herb Andrographis paniculata by Micheller Electrokinetic Capillary Chromatography", 2002, vol. 13, pp. 222-227 (Year: 2002).*
G.M. Husain et al., "Beneficial effects of a standardized Hypericum perforatum extract in rats with experimentally induced hyperglycemia," Drug Discov Ther., vol. 3, Issue 5, Oct. 2009, pp. 215-220.
M. Novelli et al., "Persistent correction of hyperglycemia in streptozotocin-nicotinamide-induced diabetic mice by a non-conventional radical scavenger," Naunyn-Schmied Arch Pharmacol, vol. 382, May 2010, pp. 127-137.
H.T. Li et al., "Antihyperglycemic Effects of Baicalin on Streptozotocin-Nicotinamide induced Diabetic Rats," Phytotherapy Research, vol. 25, Jul. 2011, pp. 189-194.
Parvez Hossain et al., "Obesity and diabetes in the developing world—A growing challenge," N. Engl. J. Med., vol. 356, Jan. 2007, pp. 213-215.
R.P. Robertson, "Chronic oxidative stress as a central mechanism for glucose toxicity in pancreatic islet beta cells in diabetes," J Biol Chem., vol. 279, Issue 41, Jul. 2004, pp. 42351-42354.
S.E. Kahn, "The relative contributions of insulin resistance and beta-cell dysfunction to the pathophysiology of type 2 diabetes," Diabetologia, vol. 46, Jan. 2003, pp. 3-19.
S.E. Kahn, "The importance of β-cell failure in the development and progression of type 2 diabetes," The Journal of Clinical Endocrinology & Metabolism, vol. 86, Issue 9, Sep. 1, 2001, pp. 4047-4058.
M Prentki et al., "Islet β cell failure in type 2 diabetes," J Clin Invest., vol. 116, Issue 7, Jul. 2006, pp. 1802-1812.
T.J. Hsieh et al., "Anti-diabetic properties of non-polar Toona sinensis Roem extract prepared by supercritical-CO2 fluid," Food and Chemical Toxicology, vol. 50, Mar. 2012, pp. 779-789.

(Continued)

*Primary Examiner* — Bahar Craigo
(74) *Attorney, Agent, or Firm* — JCIP Global Inc.

(57) ABSTRACT

A method of using Neoandrographolide for lowering blood sugar, lowering blood lipid, improving liver function and improving renal function. The method includes preparing a composition comprising Neoandrographolide as the active ingredient, and administering the composition to lower the blood sugar or blood lipid of a user, to prevent a decrease in liver function of a user, or to improve the renal function of a user. The Neoandrographolide is the only active ingredient in the composition.

5 Claims, 9 Drawing Sheets

(56) References Cited

OTHER PUBLICATIONS

Arvind S. Negi et al., "Recent Advances in Plant Hepatoprotevtives: A Chemical and Biological Profile of Some Important Leads," Medicinal Research Reviews, vol. 28, Issue 5, Sep. 2008, pp. 746-772.
Aysel Guven et al., "Effects of melatonin on streptozotocin-induced diabetic liver injury in rats," Acta Histochemica, vol. 108, Issue 2, Jul. 10, 2006, pp. 85-93.
"Office Action of Taiwan Counterpart Application", dated Nov. 25, 2020, p. 1-p. 7.
Ramesh Chander et al., "Antihepatotoxic Activity of Diterpenes of Andrographis Paniculata (Kal-Megh) Against Plasmodium Berghei-Induced Hepatic Damage in Mastomys Natalensis," International Journal of Pharmacognosy, vol. 33, No. 2, 1995, pp. 135-138.
Arvind S. Negi et al., "Recent advances in plant hepatoprotectives: a chemical and biological profile of some important leads," Medicinal Research Reviews, vol. 28, No. 5, Sep. 2008, pp. 746-772.
"Office Action of Taiwan Counterpart Application", dated Aug. 24, 2020, p. 1-p. 6.

\* cited by examiner

METHOD OF USING NEOANDROGRAPHOLIDE FOR LOWERING BLOOD SUGAR, LOWERING BLOOD LIPID, IMPROVING LIVER FUNCTION AND IMPROVING RENAL FUNCTION

CROSS-REFERENCE TO RELATED APPLICATION

This application claims the priority benefit of Taiwan application serial no. 107121756, filed on Jun. 25, 2018, Taiwan application serial no. 107121758, filed on Jun. 25, 2018, and Taiwan application serial no. 107121759, filed on Jun. 25, 2018. The entirety of each of the above-mentioned patent applications is hereby incorporated by reference herein and made a part of this specification.

BACKGROUND

Technical Field

The present invention relates to a method of using Neoandrographolide. In particular, the present invention relates to a method of using Neoandrographolide in lowering blood sugar, for lowering blood lipid, for improving liver function, and for improving renal function.

Description of Related Art

Diabetes mellitus is a growing problem that causes significant financial burdens, which declines the life quality of many nationals in developed and developing countries. Diabetes is characterized by hyperglycemia in patients and is often accompanied by metabolic disorders related with fat and protein. In general, if left untreated, diabetes can cause many complications, such as cardiovascular disease, blindness, kidney failure, and peripheral nerve damage etc. In severe cases, it may even cause death. According to statistics from the World Health Organization (WHO), there are currently about 250 million people with diabetes worldwide, and by 2030, the number of patients is estimated to reach 360 million.

Diabetes can be divided into two types, including type 1 diabetes (insulin-dependent diabetes) and type 2 diabetes (non-insulin-dependent diabetes). Both types of diabetic patients are characterized by a long-term higher than normal blood glucose levels. Other than insufficient insulin secretion or even no secretion, insulin resistance is also considered to be one of the common causes of such disease.

In the current study, the inventors have found that the plant *Andrographis paniculata* (AP) belonging to the family Acanthaceae, may be potentially used for treating diabetes, or diabetes related complications. *Andrographis paniculata* (AP) is generally used for the treatment of hyperglycemia, and is widely cultivated in India, China, and Malaysia. The main medicinal parts of *Andrographis paniculata* are the dry stems and leaves. The leaves of *Andrographis paniculata* contain a variety of diterpene lactone compounds, including Deoxyandrographolide, Andrographolide, Neoandrographolide, Homoandrographolide and Panicolide. The leaves also contain Andrographan, Andrographon, Andrographosterin, β-sitosterol-D-glucoside and the like. In addition to the Andrographolide, the root also contains 5-hydroxy-7, 8, 2", 3"-tetramethoxyflavone (Mono-o-methylwithtin), 5-hydroxy-7, 8, 2"-trimethoxyflavone (Andrographin), 5, 2"-di-hydroxy-7, 8-dimethoxyflavone (Panicolin), apigenin-7, 4"-dimethyl ether, al-sitosterol and potassium dihydrogen phosphate ($KH_2PO_4$), and the like. According to preliminary analysis, *Andrographis paniculata* also contains phenolic substances such as sterol saponins, sugars and condensed tannins.

Whether the various components of the *Andrographis paniculata* plant, especially Neoandrographolide, have specific health care functions is a topic worthy of further discussion and research.

SUMMARY

The present invention provides a novel use of Neoandrographolide, in particularly, the use of Neoandrographolide for the preparation of a composition capable of lowering blood sugar, lowering blood lipid, improve liver function and improve renal function. It has been found through experiments that the Neoandrographolide has at least the ability to simultaneously lower blood sugar, lower blood lipid, improve liver function, and improve renal function.

According to some embodiments of the invention, a method of using Neoandrographolide for lowering blood sugar is described. The method includes: preparing a composition comprising Neoandrographolide as the active ingredient; and administering the composition to lower the blood sugar of a user.

In some embodiments of the invention, the composition is administered to lower a fasting blood glucose level of the user. In some embodiments of the invention, the composition is administered to lower a glycated hemoglobin index of the user. In some embodiments of the invention, the composition is administered to increase a glucose tolerance of the user. In some embodiments of the invention, the Neoandrographolide is the only active ingredient in the composition. In some embodiments of the invention, the composition is administered with a minimum effective dose of the Neoandrographolide, and the minimum effective dose of the Neoandrographolide is in a range of 0.5 mg/kg to 20 mg/kg. In some embodiments of the invention, the composition is administered with a minimum effective dose of the Neoandrographolide, and the minimum effective dose of the Neoandrographolide is in a range of 0.625 mg/kg to 20 mg/kg. In some embodiments of the invention, the composition further comprises additives, carriers, diluents or excipients used as inactive ingredients in the composition.

According to some other embodiments of the invention, a method of using Neoandrographolide for lowering blood lipid is described. The method includes: preparing a composition comprising Neoandrographolide as the active ingredient; and administering the composition to lower the blood lipid of a user.

In some embodiments of the invention, the composition is administered to lower the triglyceride levels of the user. In some embodiments of the invention, the composition is administered to lower the total cholesterol levels in the blood of the user. In some embodiments of the invention, the Neoandrographolide is the only active ingredient in the composition. In some embodiments of the invention, the composition is administered with a minimum effective dose of the Neoandrographolide, and the minimum effective dose of the Neoandrographolide is in a range of 0.5 mg/kg to 20 mg/kg. In some embodiments of the invention, the composition is administered with a minimum effective dose of the Neoandrographolide, and the minimum effective dose of the Neoandrographolide is in a range of 0.625 mg/kg to 20 mg/kg. In some embodiments of the invention, the composition further comprises additives, carriers, diluents or excipients used as inactive ingredients in the composition.

According to some other embodiments of the invention, a method of using Neoandrographolide for improving liver function is described. The method includes: preparing a composition comprising Neoandrographolide as the active ingredient; and administering the composition to prevent a decrease in liver function of a user.

In some embodiments of the invention, the Neoandrographolide is used to lower the aspartate aminotransferase index in the blood of the user. In some embodiments of the invention, the Neoandrographolide is the only active ingredient in the composition. In some embodiments of the invention, the composition is administered with a minimum effective dose of the Neoandrographolide, and the minimum effective dose of the Neoandrographolide is in a range of 1.25 mg/kg to 10 mg/kg. In some embodiments of the invention, the composition further comprises additives, carriers, diluents or excipients used as inactive ingredients in the composition.

According to yet another embodiment of the invention, a method of using Neoandrographolide for improving renal function is described. The method includes: preparing a composition comprising Neoandrographolide as the active ingredient; and administering the composition to improve the renal function of a user.

In some embodiments of the invention, the composition is administered to lower a creatinine index of the user to improve renal clearance. In some embodiments of the invention, the composition is administered to lower a uric acid index of the user. In some embodiments of the invention, the Neoandrographolide is the only active ingredient in the composition. In some embodiments of the invention, the composition is administered with a minimum effective dose of the Neoandrographolide, and the minimum effective dose of the Neoandrographolide is in a range of 0.5 mg/kg to 20 mg/kg. In some embodiments of the invention, the composition is administered with a minimum effective dose of the Neoandrographolide, and the minimum effective dose of the Neoandrographolide is in a range of 0.625 mg/kg to 20 mg/kg. In some embodiments of the invention, the user is a patient with type 2 diabetes.

In the above embodiments, the composition is a pharmaceutical composition or a formulation. In some embodiments, the formulation is in the form of troches, tablets, liquids, powders, granules, disintegrants, pills, drops, dropping pills, capsules, ointments, creams, latex, gels, patch, injections, inhalations, spray or suppositories. In some embodiments, the formulation is a topical formulation, and the topical formulation is a liquid, powder, granule, spray, ointment, cream, latex, gel or patch. In some embodiments, the formulation is an oral formulation, and the oral formulation include capsules, troches, pills, granules, disintegrants, drops, and dropping pills. In some embodiments, the composition further comprises a flavor enhancer, sweetener, thickener or excipient used in food products (health food products) as an inactive ingredient in the composition.

According to the above, the present invention provides a novel use of Neoandrographolide for lowering blood sugar, lowering blood lipid, for improving liver function and improving renal function.

DESCRIPTION OF THE EMBODIMENTS

Figure 1:
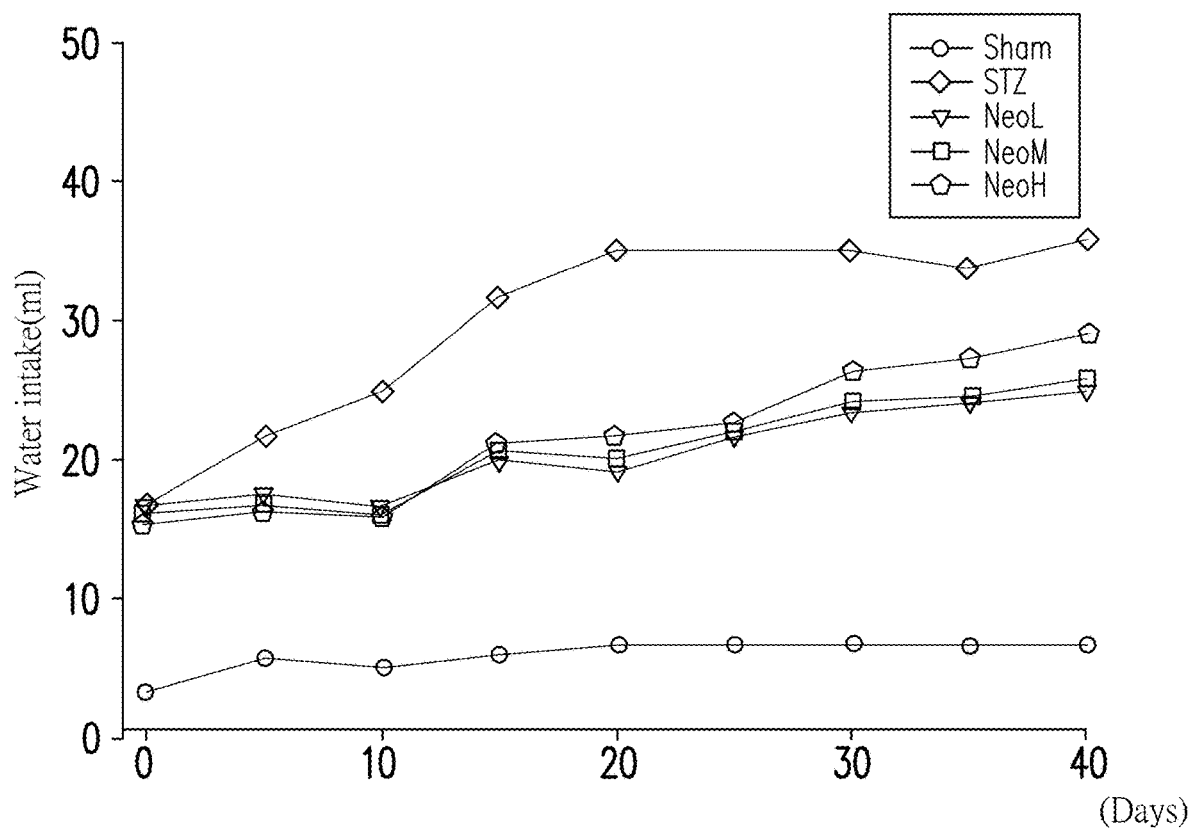
FIG. 1 is a graph showing the results of a water intake test of various doses of Neoandrographolide for type 2 diabetic mouse induction groups in the experimental examples of the present invention.

The Neoandrographolide described in the examples of the present invention may include Neoandrographolide extracted from *Andrographis paniculata* or a Neoandrographolide obtained through chemical synthesis. The chemical structure of the Neoandrographolide is shown in chemical formula 1 below:

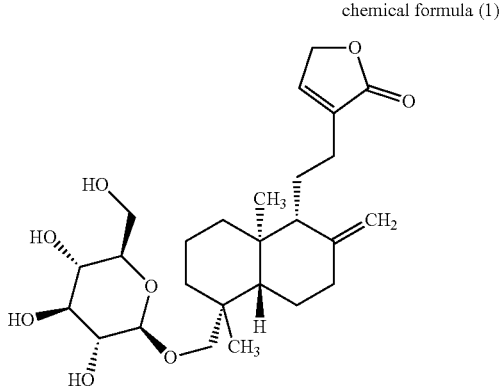 [SMILES: C=C1CC[C@@H]2[C@](C)(CO[C@@H]3O[C@H](CO)[C@@H](O)[C@H](O)[C@H]3O)CCC[C@@]2(C)[C@@H]1CCC1=CCOC1=O]

chemical formula (1)

The Neoandrographolide described in the examples of the present invention comprises physiologically functional derivatives thereof. In other words, the Neoandrographolide described in the examples of the present invention comprises the pharmaceutically acceptable salt thereof, the pharmaceutically acceptable enantiomers, the pharmaceutically acceptable solid forms (crystalline, semi-crystalline or amorphous), the pharmaceutically acceptable polymorphs, the pharmaceutically acceptable solvates or the pharmaceutically acceptable metabolites or pharmaceutically acceptable prodrugs thereof.

The different functions of Neoandrographolide for lowering blood sugar, lowering blood lipid, for improving liver function and improving renal function will be briefly described below.

Neoandrographolide for Lowering Blood Sugar:

Some embodiments of the present invention provide the use of Neoandrographolide to prepare a composition for modulating hypoglycemic properties, the composition comprising Neoandrographolide as the only pharmacologically active ingredient. According to an embodiment of the invention, administration of the composition can effectively reduce the fasting blood glucose value of the applicator (i.e., the user). According to an embodiment of the invention, administration of the composition can effectively reduce the glycated hemoglobin index of the user. According to an embodiment of the invention, administration of the composition can effectively increase glucose tolerance in a user. Through the various applications described above, the use of the composition can more effectively achieve the effect of blood glucose regulation in the user. In some other embodiments, the Neoandrographolide is the primary active ingredient in the composition, but can still be used with other active ingredients and used to achieve blood glucose regulation.

In some embodiments, when Neoandrographolide is used to lower the fasting blood glucose level of the user, the applicable dosage is from 0.5 mg/kg to 20 mg/kg. That is, its minimum effective dose is about 0.5 mg/kg. In some embodiments, the effective dosage of Neoandrographolide ranges from 0.625 mg/kg to 20 mg/kg. In some embodiments, the effective dosage of Neoandrographolide ranges from 0.625 mg/kg to 10 mg/kg. In some embodiments, the effective dosage of Neoandrographolide ranges from 0.625 mg/kg to 5 mg/kg. In another embodiment, when Neoandrographolide is used to lower the glycated hemoglobin index of the user, the applicable dose is from 0.5 mg/kg to 20 mg/kg. That is, the minimum effective dose is about 0.5 mg/kg. In some embodiments, the effective dosage of Neoandrographolide ranges from 0.625 mg/kg to 20 mg/kg. In some embodiments, the effective dosage of Neoandrographolide ranges from 0.625 mg/kg to 10 mg/kg. In some embodiments, the effective dosage of Neoandrographolide ranges from 0.625 mg/kg to 5 mg/kg. In some embodiments of the invention, the Neoandrographolide is the only active ingredient in the composition. In other words, in some embodiments of the present invention, the composition of the present embodiment uses only Neoandrographolide as the pharmacologically active ingredient, and other components contained in the extract of *Andrographis paniculata*, such as Deoxyandrographolide or Andrographolide are not included in the compositions of the present examples.

Neoandrographolide for Lowering Blood Lipid:

Some embodiments of the present invention provide the use of Neoandrographolide to prepare a composition for lowering the blood lipids, the composition comprising Neoandrographolide as the only pharmacologically active ingredient. According to an embodiment of the invention, administration of the composition can effectively reduce the triglyceride values of the applicator (i.e., the user). According to an embodiment of the invention, administration of the composition can effectively reduce the total cholesterol values of the user. Through the various applications described above, the use of the composition can more effectively achieve the effect of lowering the blood lipid in the user. In some other embodiments, the Neoandrographolide is the primary active ingredient in the composition, but can still be used with other active ingredients and used to achieve blood glucose regulation.

In some embodiments, when Neoandrographolide is used to lower the triglyceride value in the blood of the user, the applicable dosage is from 2.5 mg/kg to 20 mg/kg. That is, its minimum effective dose is about 2.5 mg/kg. In another embodiment, when Neoandrographolide is used to lower the total cholesterol value in the blood of the user, the applicable dose is from 2.5 mg/kg to 20 mg/kg. That is, the minimum effective dose is about 2.5 mg/kg. In some embodiments of the invention, the Neoandrographolide is the only active ingredient in the composition. In other words, in some embodiments of the present invention, the composition of the present embodiment uses only Neoandrographolide as the pharmacologically active ingredient, and other components contained in the extract of *Andrographis paniculata*, such as Deoxyandrographolide or Andrographolide are not included in the compositions of the present examples.

Neoandrographolide for Improving Liver Function:

Some embodiments of the present invention provide the use of Neoandrographolide to prepare a composition that improves liver function, the composition comprises Neoandrographolide as the only pharmacologically active ingredient. According to an embodiment of the present invention, administration of the composition can effectively prevent a decrease in liver function of an applicator (i.e., a user). According to an embodiment of the invention, administration of the composition can effectively reduce the aspartate aminotransferase index in the blood of the user. Through the various applications described above, the composition can more effectively achieve the use of improving the liver function of the user. In some other embodiments, the Neoandrographolide is the primary active ingredient in the composition, but can still be used with other active ingredients to achieve the effect of improving liver function.

In some embodiments, when Neoandrographolide is used to avoid a decrease in liver function of the user, the applicable dose is from 1.25 mg/kg to 10 mg/kg. That is, its minimum effective dose is about 1.25 mg/kg. In some embodiments, the effective dosage of Neoandrographolide ranges from 1.25 mg/kg to 10 mg/kg. In some embodiments, the effective dosage of Neoandrographolide ranges from 2.5 mg/kg to 5 mg/kg. In another embodiment, when Neoandrographolide is used to lower the aspartate aminotransferase index in the blood of a user, the applicable dose is from 1.25 mg/kg to 10 mg/kg. That is, its minimum effective dose is about 1.25 mg/kg. In some embodiments, the effective dosage of Neoandrographolide ranges from 1.25 mg/kg to 10 mg/kg. In some embodiments, the effective dosage of Neoandrographolide ranges from 2.5 mg/kg to 5 mg/kg. In some embodiments of the invention, the Neoandrographolide is the only active ingredient in the composition. In other words, in some embodiments of the present invention, the composition of the present embodiment uses only Neoandrographolide as the pharmacologically active ingredient, and other components contained in the extract of *Andrographis paniculata*, such as Deoxyandrographolide or Andrographolide are not included in the compositions of the present examples.

Neoandrographolide for Improving Renal Function:

Some embodiments of the present invention provide the use of Neoandrographolide to prepare a composition that improves renal function, the composition comprises Neoandrographolide as the only pharmacologically active ingredient. According to an embodiment of the invention, administration of the composition can effectively reduce the creatinine index of the applicator (i.e., the user) to improve renal clearance. According to an embodiment of the invention, administration of the composition can effectively reduce the uric acid index of the user. Through the various applications described above, the composition can more effectively achieve the use of improving the renal function of the user. In some other embodiments, the Neoandrographolide is the primary active ingredient in the composition, but can still be used with other active ingredients to achieve the effect of improving renal function.

In some embodiments, when Neoandrographolide is used to lower the creatinine index of the user to improve renal clearance, the applicable dosage is from 0.5 mg/kg to 20 mg/kg. That is, its minimum effective dose is about 0.5 mg/kg. In some embodiments, the effective dosage of Neoandrographolide ranges from 0.625 mg/kg to 20 mg/kg. In some embodiments, the effective dosage of Neoandrographolide ranges from 0.625 mg/kg to 10 mg/kg. In some embodiments, the effective dosage of Neoandrographolide ranges from 0.625 mg/kg to 5 mg/kg. In another embodiment, when Neoandrographolide is used to lower the uric acid index of the user, the suitable dosage is from 0.5 mg/kg to 20 mg/kg. That is, its minimum effective dose is about 0.5 mg/kg. In some embodiments, the effective dosage of Neoandrographolide ranges from 0.625 mg/kg to 20 mg/kg. In some embodiments, the effective dosage of Neoandrographolide ranges from 0.625 mg/kg to 10 mg/kg. In some embodiments, the effective dosage of Neoandrographolide ranges from 0.625 mg/kg to 5 mg/kg. In some embodiments of the invention, the Neoandrographolide is the only active ingredient in the composition. In other words, in some embodiments of the present invention, the composition of the present embodiment includes only Neoandrographolide as the pharmacologically active ingredient, and other components contained in the extract of *Andrographis paniculata*, such as Deoxyandrographolide or Andrographolide are not included in the compositions of the present examples.

In the above embodiments, the composition is a pharmaceutical composition or a formulation. In some embodiments, the formulation may be an oral formulation or a topical formulation, but is not limited thereto. In some embodiments, the formulation is in the form of troches, tablets, liquids, powders, granules, disintegrants, pills, drops, dropping pills, capsules, ointments, creams, latex, gels, patch, injections, inhalations, spray or suppositories, etc. In some embodiments, the oral formulation refers to those formulation that may be taken orally, or may be suitable for oral administration. For the purposes of the present invention, oral formulations include capsules, troches, pills, granules, disintegrants, drops, and dropping pills. For example, the formulation may be coated or uncoated, foamed, soluble, disintegrating, enteric or sustained release tablets; sugar-coated tablets, hard capsules, soft capsules, granule form, pills, tablet forms blended compositions. Preferably, the oral formulation is in the form of a troche or capsule. In some embodiments, the topical formulation is a liquid, powder, granule, spray, ointment, cream, latex, gel or patch.

In some embodiments, the composition is a health food composition, a functional food composition, a functional health food composition, or even a food composition that can be used for preventive change in physiological function, or a food composition having appearance changing function etc., but is not limited thereto. In some embodiments, the food composition further comprises an additive, carrier, diluent or excipient used as the other inactive ingredient in the composition. The carrier, diluent or excipient is not particularly limited, and may be adjusted in combination with different composition types or dosage forms. For example, additives and excipients include, but are not limited to, anti-sticking agents, anti-foaming agents, buffers, polymers, antioxidants, preservatives, chelating agents, viscosity modifiers, tonicity modifiers, flavoring agents, coloring agents, fragrances, opacifiers, suspending agents, binders, fillers, plasticizers, lubricants, and mixtures thereof. In some embodiments, the composition further comprises a flavor enhancer, sweetener, thickener or excipient used in food products as an inactive ingredient in the composition.

In some embodiments, functional food for blood glucose regulation, functional food for lowering blood lipid, functional food for improving renal function, functional food for improving liver function, may use a composition consisting of Neoandrographolide or a composition comprising Neoandrographolide as the main active ingredient. In some embodiments, the functional food product may be presented in the form of a liquid beverage, gelatin, capsule, troche, tablet or powder, but is not limited thereto. For example, the functional food can be any functional food that can be taken or consumed by oral administration.

The application and effects of Neoandrographolide in the embodiments of the present invention will be exemplified by the following examples. However, the following examples are merely illustrative and are not intended to limit the invention.

EXAMPLES

In the following examples, various doses of Neoandrographolide will be tested and evaluated for its effect of blood glucose regulating ability, physiological function, blood biochemical substance and some important organ histopathology in the induction group (induced type 2 diabetic mice).

Male ICR mice (19-21 g) were obtained from BioLASCO Taiwan Co., Ltd. The mice were kept in the animal center of Transworld University at a controlled temperature of 22±2° C., relative humidity 55±5%, and with 12 hour light/12 hour dark cycles for 1 week before the experiment. For the induction of type 2 diabetic mice (induction treatment group STZ), Nicotinamide (210 mg/kg b.w.) (Sigma, Saint Louis, Mo., USA), dissolved in saline was intraperitoneally injected into mice. After 15 minutes, the mice were administered with streptomycin (STZ) (Sigma, 180 mg/kg bw, ip injection), which was dissolved in citrate buffer (pH 4.5) before use. The control group received both vehicles. During the experimental period, the animals' food intake and body weight were monitored once a week. In addition, the dosage of the Neoandrographolide (Sigma-Aldrich Chemical Co., Missouri, USA) of the present invention is: NeoL (low dose group of Neoandrographolide): Neoandrographolide 2.5 mg/kg; NeoM (middle dose group of Neoandrographolide): Neoandrographolide 5.0 mg/kg; NeoH (high dose group of Neoandrographolide): Neoandrographolide 10 mg/kg. The above active ingredient was dissolved in Tween 20 and adjusted to a 0.5% methylcellulose (CMC) solution. The blank group (Sham) was normal mice without induction treatment.

Clinical Observations

Animals were observed at least twice a day (time interval of each observation is not less than six hours), to determine the animal health or death situation. At least once daily to observe the clinical symptoms of the test animal, recorded the toxic effects showed on test animals, including the beginning and the process of the effects. After completion of the test, surviving animals were sacrificed; before necropsy, blood samples were collected for serum biochemistry.

Example 1: Preliminary Water Intake Test

In general, diabetic patients usually have clinical symptoms of "drinking more water." In this experimental example, the water intake was recorded in a 40-day period for the blank group Sham, the induction treatment group STZ, Neoandrographolide low dose group NeoL (2.5 mg/kg), Neoandrographolide middle dose group NeoM (5.0 mg/kg) and Neoandrographolide high dose group NeoH (10 mg/kg). The experimental results are shown in FIG. 1.

FIG. 1 is a graph showing the results of a water intake test of various doses of Neoandrographolide for type 2 diabetic mouse induction groups in the experimental examples of the present invention. As shown in FIG. 1, the water intake of the mice in the induction treatment group STZ was significantly higher than that of the blank group Sham in the period of 40 days. The results of this experiment demonstrate that the water intake of induced type 2 diabetic mice is much higher than that of normal mice. In addition, when the induced type 2 diabetic mice were administered with different doses of Neoandrographolide, results showed that in both high dose (10 mg/kg) and low dose (2.5 mg/kg) of Neoandrographolide, the amount of water intake in the induced type 2 diabetic mice was significantly reduced. In other words, Neoandrographolide can be used alone as an active ingredient to alleviate the clinical signs of diabetic mice.

Example 2: Neoandrographolide for Lowering Blood Sugar

The following evaluation are performed to prove that Neoandrographolide is effective in lowering blood sugar, or be used for blood sugar control.

Oral Glucose Tolerance Test

In this experimental example, an oral glucose tolerance test was performed to evaluate peripheral glucose utilization. After administering the Neoandrographolide low dose group NeoL (2.5 mg/kg), the Neoandrographolide middle dose group NeoM (5.0 mg/kg) and the Neoandrographolide high dose group NeoH (10 mg/kg) for 30 minutes, a blood sample is taken before glucose administration to determine the blood glucose concentration in the sample, which represent the blood glucose level at 0 hours. After glucose (2 g/kg) was administered for 30, 60, 90, 120, 150, and 180 minutes, blood samples were collected to determine the blood glucose concentration in the samples. The experimental results are shown in FIG. 2.

Figure 2:
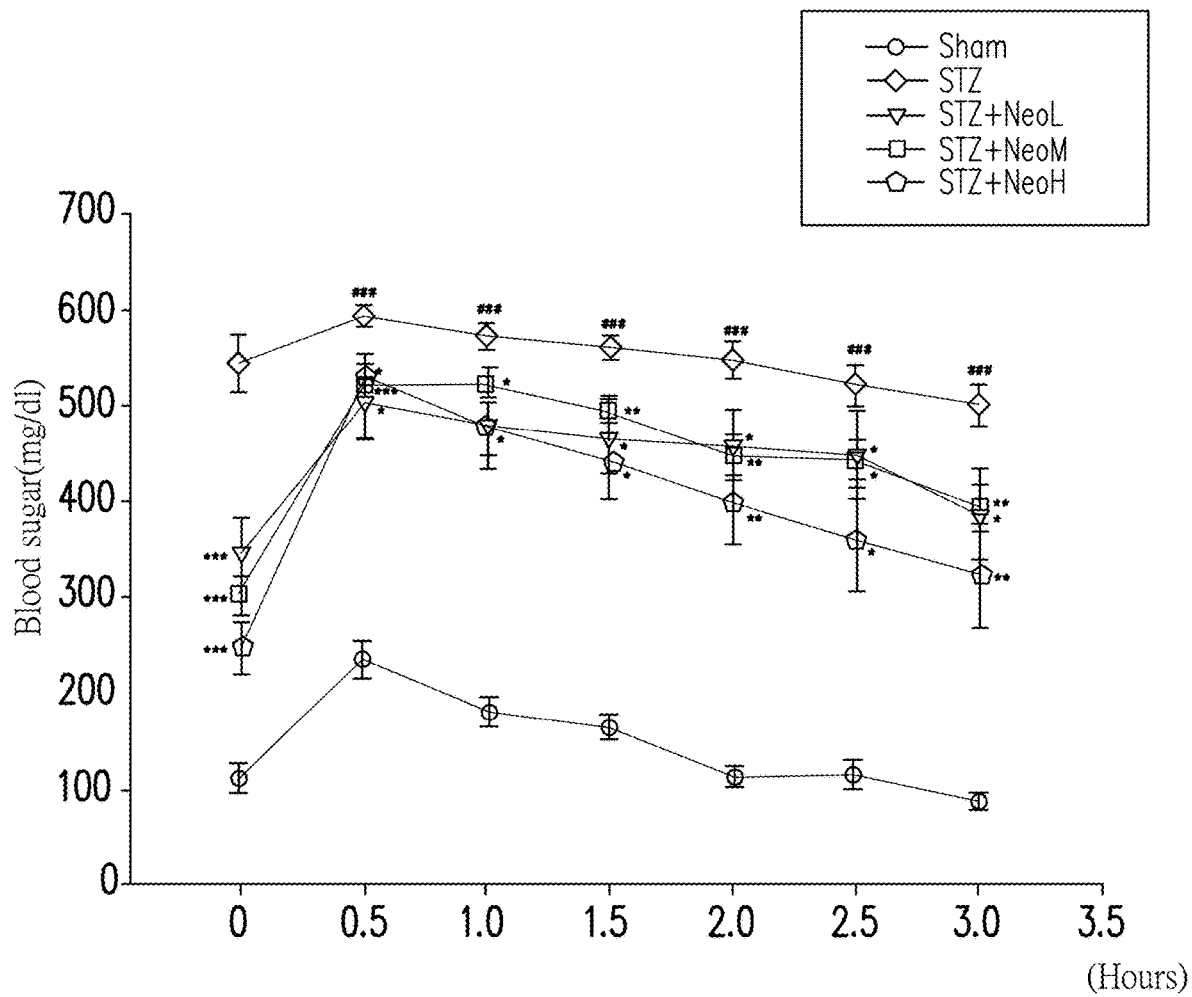
FIG. 2 is a graph showing the results of an oral glucose tolerance test of various doses of Neoandrographolide for type 2 diabetic mouse induction groups in the experimental examples of the present invention.

FIG. 2 is a graph showing the results of an oral glucose tolerance test of various doses of Neoandrographolide for type 2 diabetic mouse induction groups in the experimental examples of the present invention. In FIG. 2, the respective values are expressed as mean±SEM (standard error of mean), where $^{\#\#\#}P<0.001$ is compared with the blank group Sham; *P<0.05, P<0.01, *P<0.001 are compared to the induction treatment group STZ. As shown in the experimental results of FIG. 2, the blood glucose value of the mice in the induction treatment group STZ is significantly higher than that of the blank group Sham. These experimental results prove that the glucose tolerance in induced type 2 diabetic mice is worse than that in normal mice. In addition, the three dose groups of Neoandrographolide (NeoL, NeoM, NeoH) showed significantly lower blood glucose levels than the induction treatment group STZ within 0 to 3 hours. The Neoandrographolide of the present invention can be used to improve low glucose tolerance in induced type 2 diabetic mice. In other words, the Neoandrographolide of the present invention can be used to increase the glucose tolerance in induced diabetic mice.

Fasting Blood Glucose Assay

In this experimental example, the fasting blood glucose values were recorded in a 42-day period for the blank group Sham, the induction treatment group STZ, Neoandrographolide low dose group NeoL (2.5 mg/kg), Neoandrographolide middle dose group NeoM (5.0 mg/kg) and Neoandrographolide high dose group NeoH (10 mg/kg). The experimental results are shown in FIG. 3.

Figure 3:
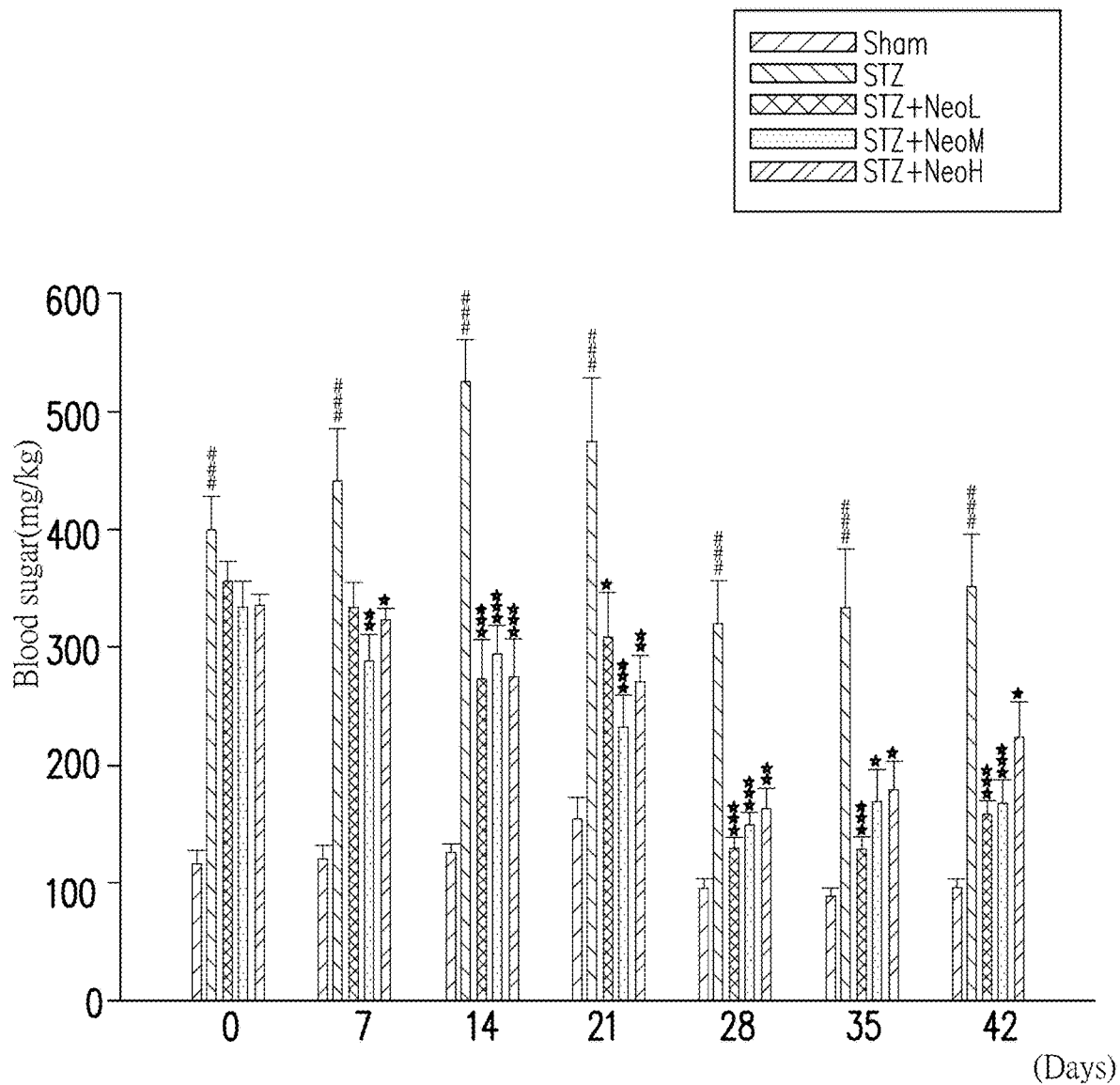
FIG. 3 is a graph showing the results of fasting blood glucose assay of various doses of Neoandrographolide for type 2 diabetic mouse induction groups in the experimental examples of the present invention.

FIG. 3 is a graph showing the results of fasting blood glucose assay of various doses of Neoandrographolide for type 2 diabetic mouse induction groups in the experimental examples of the present invention. In FIG. 3, the respective values are expressed as mean±SEM (standard error of mean), where $^{\#\#\#}P<0.001$ is compared with the blank group Sham; *P<0.05, P)<0.01, *P<0.001 are compared to the induction treatment group STZ. As shown in the experimental results of FIG. 3 the fasting blood glucose levels of the STZ mice in the induction treatment group was significantly higher than that of the blank group Sham at 0-42 days. The results of this experiment demonstrate that the glucose tolerance in induced type 2 diabetic mice is worse than that in normal mice. In addition, the three dose groups of Neoandrographolide (NeoL, NeoM, NeoH) had significantly lower fasting blood glucose values than the induction treatment group STZ seven days after administration. In other words, the Neoandrographolide of the present invention can be used to reduce the fasting blood glucose level of induced diabetic mice. From the experiments, the Neoandrographolide of the present invention can be used to reduce the fasting blood glucose levels and improve the problem of elevated blood glucose in induced type 2 diabetic mice. Moreover, from the current experiment, the minimum effective dose range of 2.5 mg/kg to 10 mg/kg for the three dose groups of Neoandrographolide (NeoL, NeoM, NeoH) are all quite effective. The minimum effective dose that can be predicted by linear extrapolation may range from 0.5 mg/kg to 20 mg/kg or between 0.625 mg/kg and 20 mg/kg.

Glycated Hemoglobin (HbA1c) Assay

Glycated hemoglobin (HbA1c) is the case where red blood cells in the human blood contain hemoglobin, and when blood glucose enters the red blood cells and combines with the hemoglobin, it forms glycated hemoglobin. The average life span of red blood cells is 120 days, and once glucose is attached onto hemoglobin, it is not easy to fall off. Therefore, checking the concentration of glycated hemoglobin in blood will reflect the blood sugar control in the last 2-3 months. The biggest difference between HbA1c and blood sugar is that the blood sugar level only represents the blood sugar status at the time of blood withdrawal, and the long-term blood sugar control needs to be reflected by HbA1c. HbA1c is an excellent indicator for detecting diabetes early. These patients generally have milder conditions, whereby the slightly higher blood glucose level often falls back to the normal range after starvation for a certain period. Therefore, when measuring blood glucose on a fasting basis, such patients are often missed, whereby HbA1c does not have such drawback. In 2009, the American Diabetes Association proposed that "glycated hemoglobin" of >=6.5% as the diagnostic criteria for diabetes. Therefore, in addition to being used as a blood glucose tracking indicator for diabetes, "glycated hemoglobin" is being used as a new diagnostic tool. In recent years, HbA1c (glycated hemoglobin) has been widely used in diabetes patients who need to monitor the blood glucose levels. It can reflect the blood sugar control status about one month before blood collection and can be used to supervise the blood sugar control situation. Furthermore, the HbA1c levels can be used as a basis for adjusting the dose of medication.

In this experimental example, the glycated hemoglobin (HbA1c) values of mice were recorded in a 42-day period after continuous administration for the blank group Sham, the induction treatment group STZ, Neoandrographolide low dose group NeoL (2.5 mg/kg), Neoandrographolide middle dose group NeoM (5.0 mg/kg) and Neoandrographolide high dose group NeoH (10 mg/kg). The experimental results are shown in FIG. 4.

Figure 4:
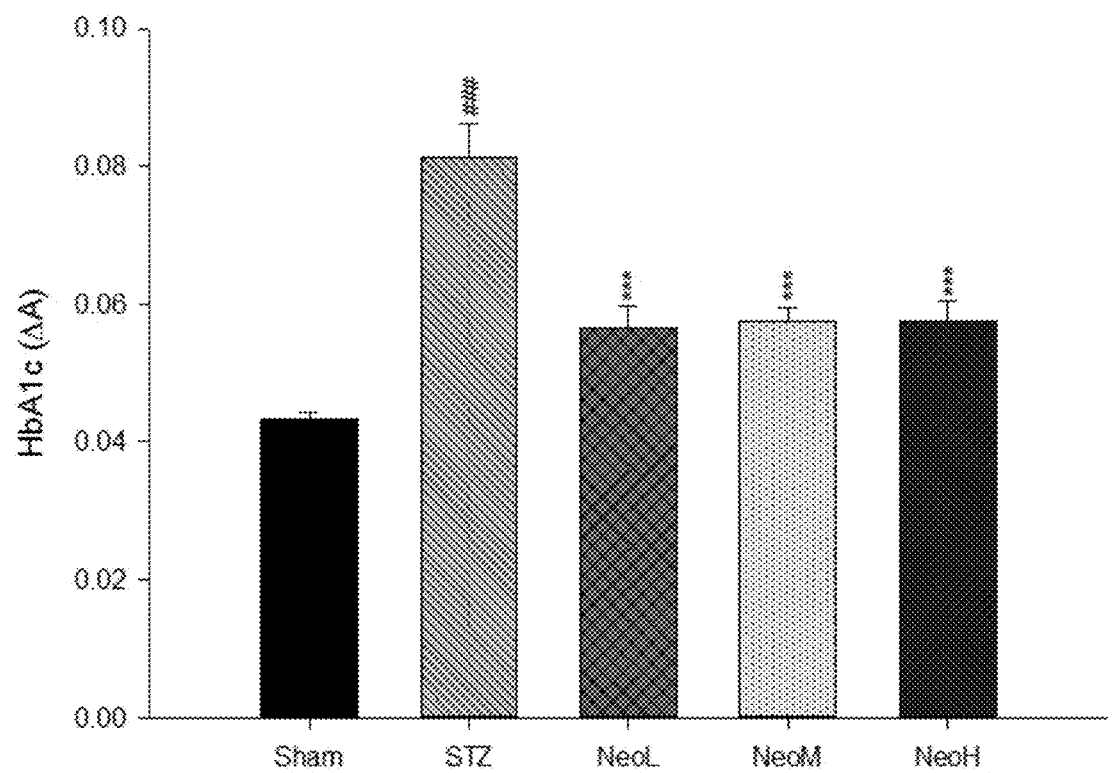
FIG. 4 is a graph showing the results of the effects of various doses of Neoandrographolide on glycated hemoglobin (HbA1c) of type 2 diabetic mouse induction groups in the experimental examples of the present invention.

FIG. 4 is a graph showing the results of the effects of various doses of Neoandrographolide on glycated hemoglobin (HbA1c) of type 2 diabetic mouse induction groups in the experimental examples of the present invention. In FIG. 4, the respective values are expressed as mean±SEM (standard error of mean), where $^{\#\#\#}P<0.001$ is compared with the blank group Sham; ***$P<0.001$ is compared to the induction treatment group STZ. As shown in the experimental results of FIG. 4, the HbA1c value of the mice in the induction treatment group STZ was significantly higher than that of the blank group Sham after 42 days. These experimental results demonstrate that the blood glucose control of induced type 2 diabetic mice is worse than that of normal mice. In addition, the HbA1c values of the three dose groups (NeoL, NeoM, NeoH) of Neoandrographolide were significantly lower than the induction treatment group STZ after 42 days of continuous administration. In other words, the Neoandrographolide of the present invention can be used to improve the problem of poor blood sugar control in induced type 2 diabetic mice. Moreover, from the current experiment, the minimum effective dose range of 2.5 mg/kg to 10 mg/kg for the three dose groups of Neoandrographolide (NeoL, NeoM, NeoH) are all quite effective. The minimum effective dose that can be predicted by linear extrapolation may range from 0.5 mg/kg to 20 mg/kg or between 0.625 mg/kg and 20 mg/kg.

Example 3: Neoandrographolide for Improving Liver Function

The following evaluation are performed to prove that Neoandrographolide is effective in improving liver function.
Aspartate Aminotransferase (AST) Assay In general, patients with type 2 diabetes are clinically associated with nonalcoholic fatty liver disease, which in turn leads to liver cell damage and decreased liver function. Aspartate aminotransferase (AST) is an enzyme found mainly in the liver, the heart muscle, the skeletal muscle and the red blood cells. When liver cells are destroyed or damaged, AST enzymes are released and enters the bloodstream. Therefore, blood tests can be used to know if liver function is affected or not.

In this experimental example, the AST index of mice were recorded in a 42-day period after continuous administration for the blank group Sham, the induction treatment group STZ, Neoandrographolide low dose group NeoL (2.5 mg/kg), Neoandrographolide middle dose group NeoM (5.0 mg/kg) and Neoandrographolide high dose group NeoH (10 mg/kg). The experimental results are shown in FIG. 5.

Figure 5:
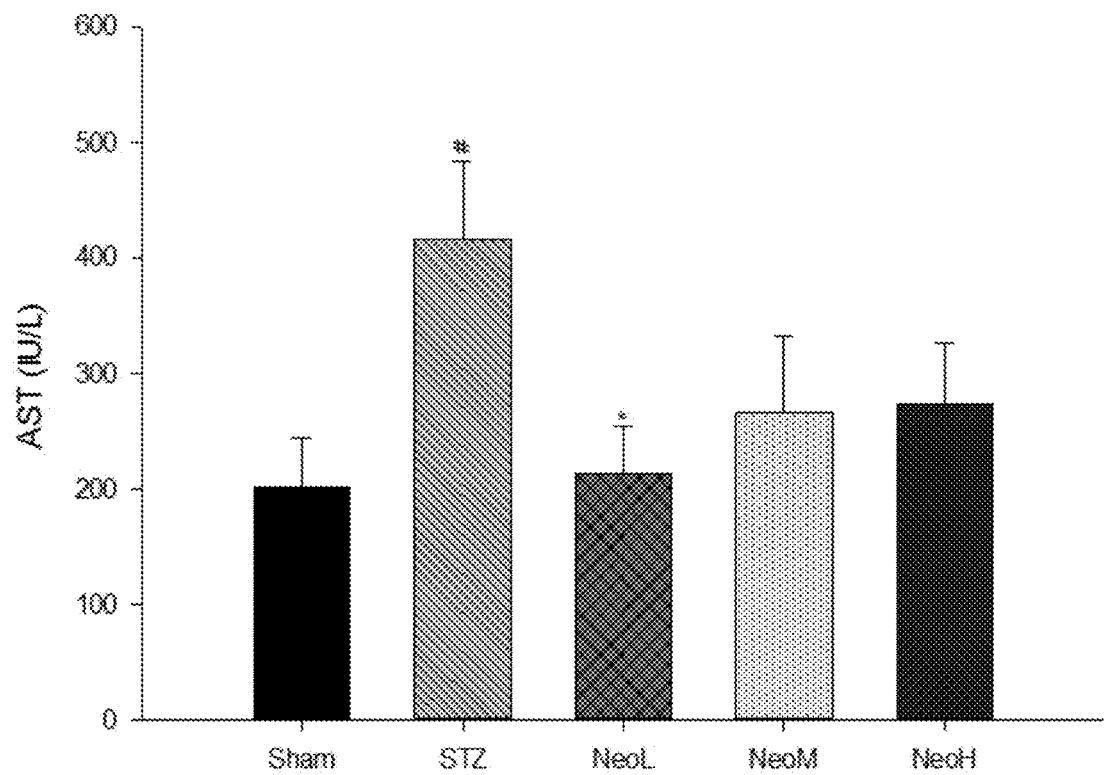
FIG. 5 is a graph showing the results of the effects of various doses of Neoandrographolide on the aspartate aminotransferase (AST) index of type 2 diabetic mouse induction groups in the experimental examples of the present invention.

FIG. 5 is a graph showing the results of the effects of various doses of Neoandrographolide on the aspartate aminotransferase (AST) index of type 2 diabetic mouse induction groups in the experimental examples of the present invention. In FIG. 5, the respective values are expressed as mean±SEM (standard error of mean), where $^{\#}P<0.05$ is compared with the blank group Sham; *$P<0.05$ is compared to the induction treatment group STZ. As shown in the experimental results of FIG. 5, the AST index of the mice in the induction treatment group STZ was significantly higher than that of the blank group Sham after 42 days. The experimental results demonstrate that the liver function of induced type 2 diabetic mice is worse than that of normal mice. In addition, the AST index of the three dose groups (NeoL, NeoM, NeoH) of Neoandrographolide were slightly lower than the induction treatment group STZ after 42 days of continuous administration. Among them, the Neoandrographolide low dose group NeoL (2.5 mg/kg) had the most significant reduction in the AST values. These experimental results indicate that the Neoandrographolide of the present invention has an effect of improving liver function, and the minimum effective dose is judged to be around 2.5 mg/kg. The minimum effective dose that can be predicted by linear extrapolation may range from 1.25 mg/kg to 10 mg/kg.

Example 4: Neoandrographolide for Lowering Blood Lipid

The following evaluation are performed to prove that Neoandrographolide is effective in lowering blood lipid.
Triglyceride and Cholesterol Assay Clinically, 60 to 80 percent of diabetic patients have hypertension and hyperlipidemia complications. The mechanism of diabetes with hyperlipidemia is more complicated, and the most common types include increased triglyceride in blood, decreased high density lipoprotein cholesterol (HDL-C) and increased low density lipoprotein cholesterol (LDL-C). Therefore, for diabetic patients, the monitoring of triglycerides and total cholesterol is also extremely important.

In this experimental example, the triglyceride values and the total cholesterol in blood of mice were recorded in a 42-day period after continuous administration for the blank group Sham, the induction treatment group STZ, Neoandrographolide low dose group NeoL (2.5 mg/kg), Neoandrographolide middle dose group NeoM (5.0 mg/kg) and Neoandrographolide high dose group NeoH (10 mg/kg). The experimental results are shown in FIG. 6 and FIG. 7.

Figure 6:
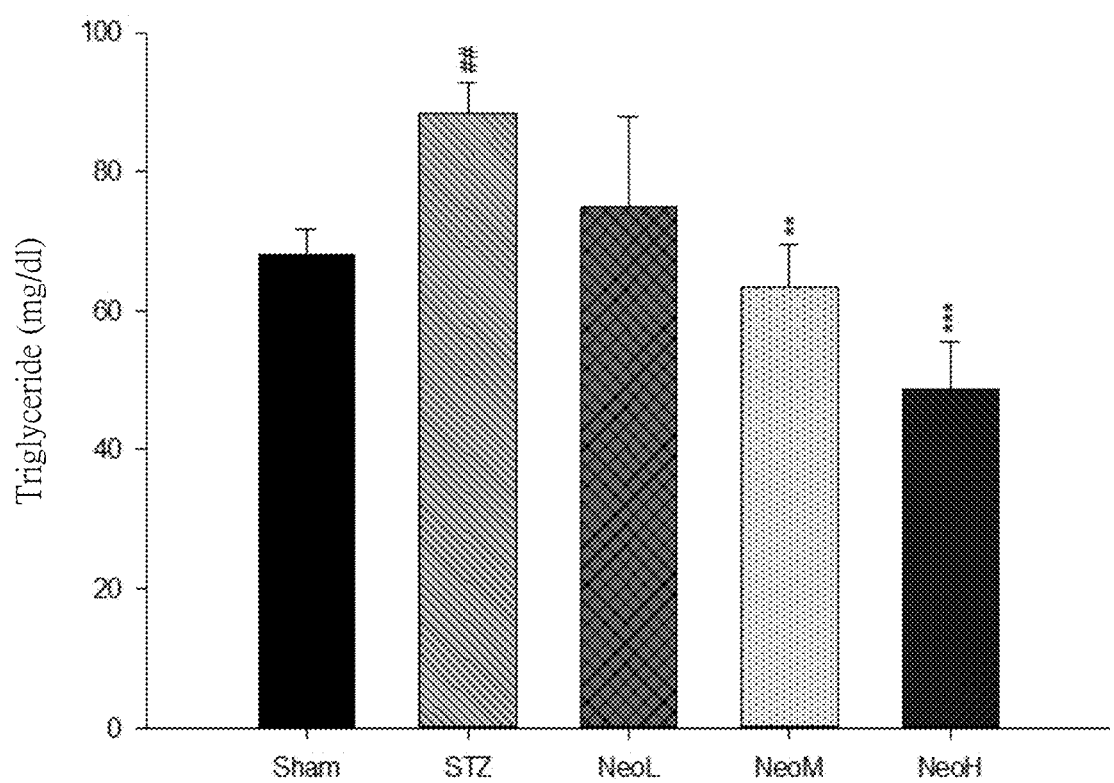
FIG. 6 is a graph showing the results of the effects of various doses of Neoandrographolide on the triglyceride values of type 2 diabetic mouse induction groups in the experimental examples of the present invention.

FIG. 6 is a graph showing the results of the effects of various doses of Neoandrographolide on the triglyceride values of type 2 diabetic mouse induction groups in the experimental examples of the present invention. In FIG. 6, the respective values are expressed as mean±SEM (standard error of mean), where $^{\#\#}P<0.01$ is compared with the blank group Sham; $P<0.01$, *$P\ 0.001$ are compared to the induction treatment group STZ. As shown in the experimental results of FIG. 6, the triglyceride value in the blood of the mice in the induction treatment group STZ was significantly higher than that of the blank group Sham after 42 days. The experimental results demonstrate that the induced type 2 diabetic mice have higher blood lipids and higher cholesterol levels. In addition, the triglyceride values of the three dose groups (NeoL, NeoM, NeoH) of Neoandrographolide were all lower than the induction treatment group STZ after 42 days of continuous administration. Among them, the Neoandrographolide middle dose group NeoM (5.0 mg/kg) and the Neoandrographolide high dose group NeoH (10 mg/kg) have the lowest triglyceride values. These experimental results indicate that the Neoandrographolide of the present invention has a triglyceride-lowering effect and this is also a dose-dependent effect, whereby the minimum effective dose is 2.5 mg/kg.

Figure 7:
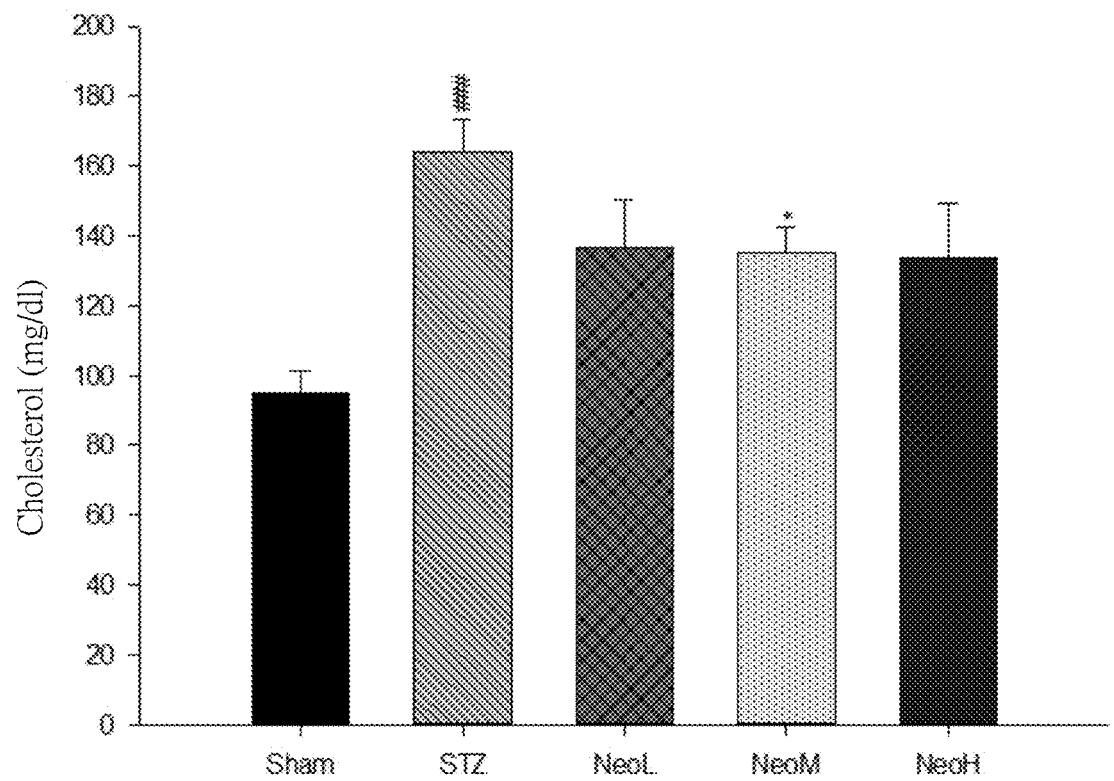
FIG. 7 is a graph showing the results of the effects of various doses of Neoandrographolide on the blood cholesterol levels of type 2 diabetic mouse induction groups in the experimental examples of the present invention.

FIG. 7 is a graph showing the results of the effects of various doses of Neoandrographolide on the blood cholesterol levels of type 2 diabetic mouse induction groups in the experimental examples of the present invention. In FIG. 7, the respective values are expressed as mean±SEM (standard error of mean), where $^{\#\#\#}P<0.001$ is compared with the blank group Sham; *P<0.05 is compared to the induction treatment group STZ. As shown in the experimental results of FIG. 7, the total cholesterol value in the blood of the mice in the induction treatment group STZ was significantly higher than that of the blank group Sham after 42 days. These experimental results demonstrate that the induced type 2 diabetic mice have higher blood lipids and higher cholesterol levels. In addition, the total cholesterol values of the three dose groups (NeoL, NeoM, NeoH) of Neoandrographolide were all lower than the induction treatment group STZ after 42 days of continuous administration. These results show that Neoandrographolide has an effect of lowering total cholesterol in the blood, and the minimum effective dose is 2.5 mg/kg.

Example 5: Neoandrographolide for Improving Renal Function

The following evaluation are performed to prove that Neoandrographolide is effective in improving renal function.

Uric Acid Assay

Many studies have found that the high-risk factors for type 2 diabetes and elevated uric acid levels are the same, wherein the most noticeable factors are overweight and obesity. Type 2 diabetes and high uric acid not only have the same pathogenic cause, but high uric acid levels can also increase the risk of developing type 2 diabetes. Therefore, lowering the level of uric acid in the blood can prevent the incidence of type 2 diabetes. There are many reasons for causing excessive uric acid in the human body. Factors such as diet, weight, exercise, medication, and genetics may cause hyperuricemia. Most of the uric acid in the blood is excreted by the kidneys. Once the uric acid value is increased, the concentration in the kidneys will also rise, and it is easy to produce uric acid crystals that precipitate in the kidneys, which causes kidney damage. Therefore, hyperuricemia is likely to cause a decline in renal function.

In this experimental example, the serum uric acid index of mice was recorded in a 42-day period after continuous administration for the blank group Sham, the induction treatment group STZ, Neoandrographolide low dose group NeoL (2.5 mg/kg), Neoandrographolide middle dose group NeoM (5.0 mg/kg) and Neoandrographolide high dose group NeoH (10 mg/kg). The experimental results are shown in FIG. 8.

Figure 8:
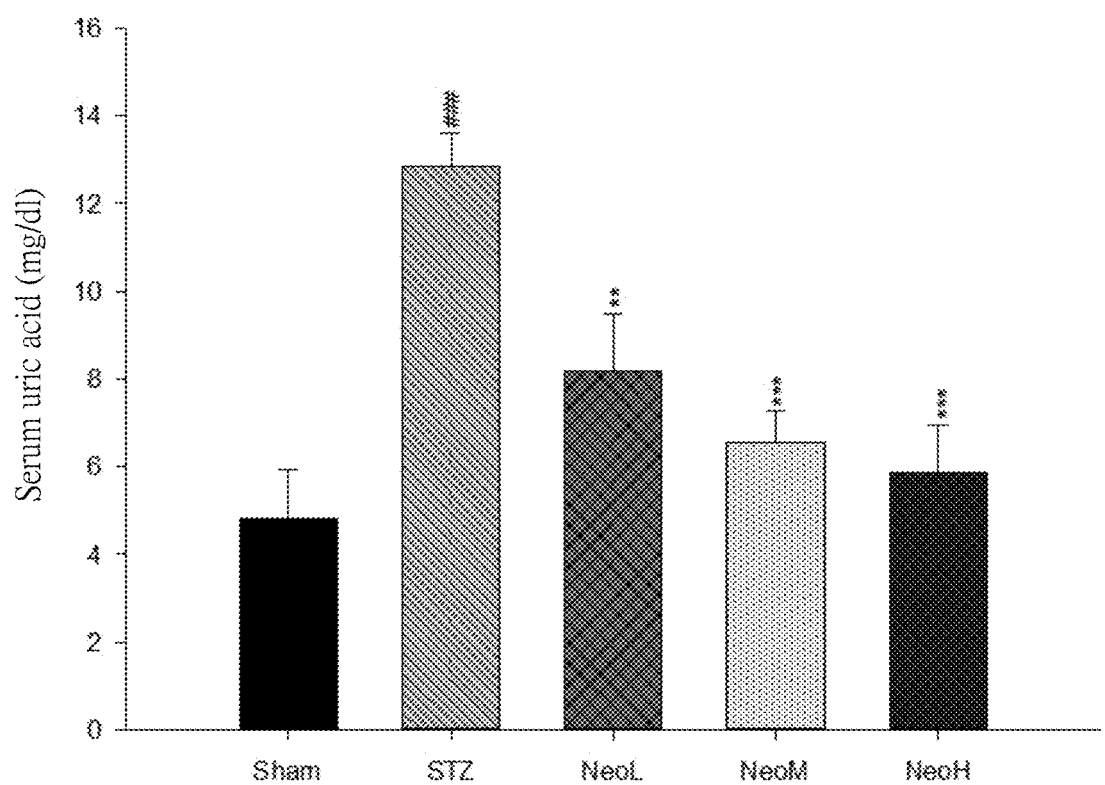
FIG. 8 is a graph showing the results of the effects of various doses of Neoandrographolide on the serum uric acid index of type 2 diabetic mouse induction groups in the experimental examples of the present invention.

FIG. 8 is a graph showing the results of the effects of various doses of Neoandrographolide on the serum uric acid index of type 2 diabetic mouse induction groups in the experimental examples of the present invention. In FIG. 8, the respective values are expressed as mean±SEM (standard error of mean), where $^{\#\#\#}P<0.001$ is compared with the blank group Sham; P<0.01, * P<0.001 are compared to the induction treatment group STZ. As shown in the experimental results of FIG. 8, the uric acid index of the mice in the induction treatment group STZ was significantly higher than that of the blank group Sham after 42 days. The experimental results demonstrate that the induced type 2 diabetic mice have a phenomenon of hyperuricemia. In addition, the serum uric acid index of the three dose groups (NeoL, NeoM, NeoH) of Neoandrographolide were significantly lower than the induction treatment group STZ after 42 days of continuous administration. These results indicate that Neoandrographolide of the present invention can reduce the uric acid index of patients with hyperuricemia and achieve an effect of improving renal function. Moreover, from the current experiment, the minimum effective dose range of 2.5 mg/kg to 10 mg/kg for the three dose groups of Neoandrographolide (NeoL, NeoM, NeoH) are all quite effective. The minimum effective dose that can be predicted by linear extrapolation may range from 0.5 mg/kg to 20 mg/kg or between 0.625 mg/kg and 20 mg/kg.

Serum Creatinine Assay

Diabetic nephropathy is one of the important complications of diabetes, which often leads to death. When the kidney disease progresses to a later stage, the filtration function will gradually be damaged, resulting in the inability to clean up harmful substances such as creatinine, which may cause an increase in creatinine and eventually lead to kidney failure. The concentration of serum creatinine in the patient can be used to determine whether the renal function is affected.

In this experimental example, the serum creatine index of mice was recorded in a 42-day period after continuous administration for the blank group Sham, the induction treatment group STZ, Neoandrographolide low dose group NeoL (2.5 mg/kg), Neoandrographolide middle dose group NeoM (5.0 mg/kg) and Neoandrographolide high dose group NeoH (10 mg/kg). The experimental results are shown in FIG. 9.

Figure 9:
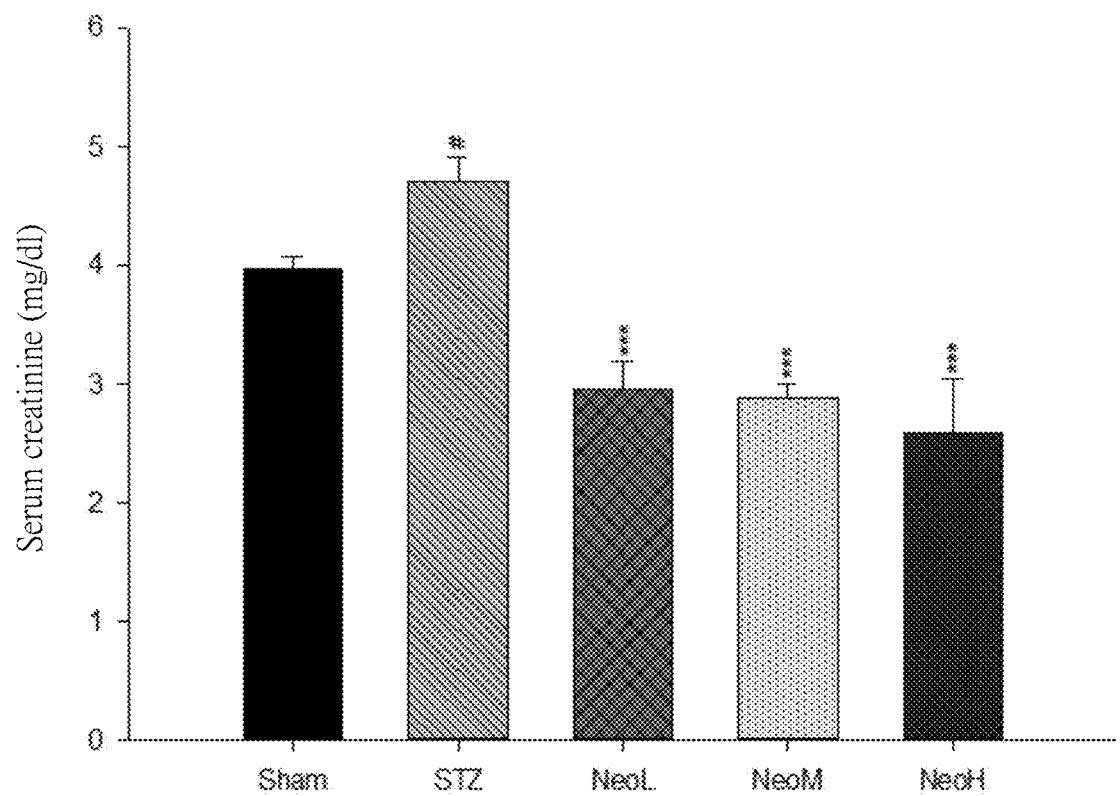
FIG. 9 is a graph showing the results of the effects of various doses of Neoandrographolide on the serum creatinine index of type 2 diabetic mouse induction groups in the experimental examples of the present invention.

FIG. 9 is a graph showing the results of the effects of various doses of Neoandrographolide on the serum creatinine index of type 2 diabetic mouse induction groups in the experimental examples of the present invention. In FIG. 9, the respective values are expressed as mean±SEM (standard error of mean), where $^{\#}P<0.05$ is compared with the blank group Sham; ***P<0.001 is compared to the induction treatment group STZ. As shown in the experimental results of FIG. 9, the serum creatinine index of the mice in the induction treatment group STZ was significantly higher than that of the blank group Sham after 42 days. These experimental results demonstrate that the renal clearance rate of the induced type 2 diabetic mice is reduced by the induction drug. In addition, the serum creatinine index of the three dose groups (NeoL, NeoM, NeoH) of Neoandrographolide were significantly lower than the induction treatment group STZ after 42 days of continuous administration. These results indicate that Neoandrographolide of the present invention can reduce the serum creatinine index of patients, thereby achieve the function of kidney protection. Moreover, from the current experiment, the minimum effective dose range of 2.5 mg/kg to 10 mg/kg for the three dose groups of Neoandrographolide (NeoL, NeoM, NeoH) are all quite effective. The minimum effective dose that can be predicted by linear extrapolation may range from 0.5 mg/kg to 20 mg/kg or between 0.625 mg/kg and 20 mg/kg.

In summary, the experimental results of the present invention showed that Neoandrographolide can individually improve the glucose tolerance of induced type 2 diabetic mice, reduce fasting blood glucose and glycosylated hemoglobin HbA1c, indicating its use in lowering blood glucose. Furthermore, Neoandrographolide alone can reduce the AST value of the induced type 2 diabetic mice, indicating its use in improving liver function. Neoandrographolide alone can also improve the triglyceride and total blood cholesterol values of induced type 2 diabetic mice, indicating its use for lowering blood lipids. In addition, Neoandrographolide alone can improve the serum uric acid index and serum creatinine index of induced type 2 diabetic mice, indicating its use of improving renal function.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A method of using neoandrographolide, comprising:
preparing a composition comprising neoandrographolide as the active ingredient; and
administering the composition to lower blood sugar, lower a fasting blood glucose level, lower a glycated hemoglobin index, and increase a glucose tolerance of a patient with type 2 diabetes, wherein the neoandrographolide is the only active ingredient in the composition,
wherein the step of administering the composition comprises administering to the patient having type 2 diabetes the neoandrographolide at a dose equivalent to 0.5 mg/kg in mice,
wherein a chemical structure of the neoandrographolide is shown in chemical formula 1 below:

chemical formula 1

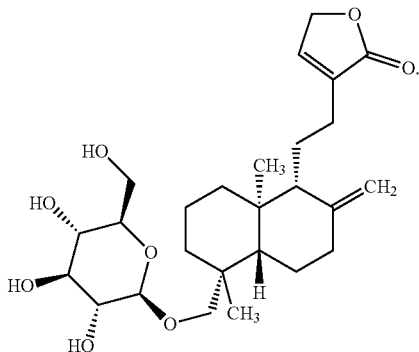

2. The method according to claim 1, wherein the composition further comprises additives, carriers, diluents or excipients used as inactive ingredients in the composition.

3. A method of using neoandrographolide, comprising:
preparing a composition comprising neoandrographolide as the active ingredient; and
administering the composition to improve liver function and for lowering the aspartate aminotransferase index in the blood of a patient with type 2 diabetes, wherein the neoandrographolide is the only active ingredient in the composition,
wherein the step of administering the composition comprises administering to the patient having type 2 diabetes the neoandrographolide at a dose equivalent to 1.25 mg/kg in mice,
wherein a chemical structure of the neoandrographolide is shown in chemical formula 1 below:

chemical formula 1

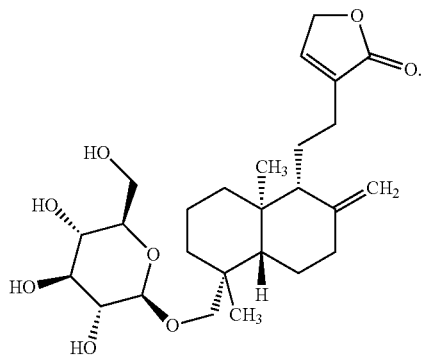

4. The method according to claim 3, wherein the composition further comprises additives, carriers, diluents or excipients used as inactive ingredients in the composition.

5. A method of using neoandrographolide, comprising:
preparing a composition comprising neoandrographolide as the active ingredient; and
administering the composition to improve the renal function and for lowering a creatinine index and lowering a uric acid index of a patient with type 2 diabetes, wherein the neoandrographolide is the only active ingredient in the composition,
wherein the step of administering the composition comprises administering to the patient having type 2 diabetes the neoandrographolide at a dose equivalent to 0.5 mg/kg in mice,
wherein a chemical structure of the neoandrographolide is shown in chemical formula 1 below:

chemical formula 1

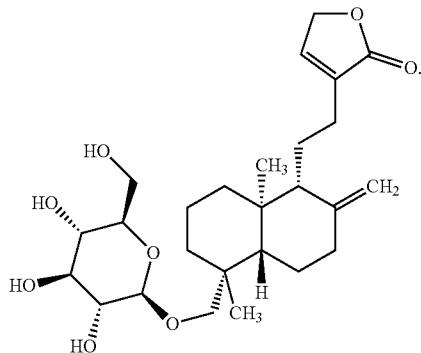

* * * * *